United States Patent
Runft et al.

(10) Patent No.: US 9,170,213 B2
(45) Date of Patent: Oct. 27, 2015

(54) SENSOR DEVICE FOR A PACKAGING MACHINE DESIGNED AS A CAPSULE FILLING AND SEALING MACHINE OR FOR A CAPSULE CONTROL DEVICE

(75) Inventors: Werner Runft, Winnenden (DE); Iulian Maga, Ludwigsburg (DE); Ralf Schmied, Freiberg (DE); Guenter Liebhart, Backnang (DE); Martin Vogt, Schorndorf (DE)

(73) Assignee: Robert Bosch GmbH, Stuttgart (DE)

( * ) Notice: Subject to any disclaimer, the term of this patent is extended or adjusted under 35 U.S.C. 154(b) by 472 days.

(21) Appl. No.: 13/502,872
(22) PCT Filed: Oct. 1, 2010
(86) PCT No.: PCT/EP2010/064616
§ 371 (c)(1), (2), (4) Date: Apr. 19, 2012
(87) PCT Pub. No.: WO2011/047945
PCT Pub. Date: Apr. 28, 2011

(65) Prior Publication Data
US 2012/0207272 A1    Aug. 16, 2012

(30) Foreign Application Priority Data

Oct. 19, 2009  (DE) .......................... 10 2009 045 809
Feb. 9, 2010   (DE) .......................... 10 2010 001 701
Jul. 28, 2010  (DE) .......................... 10 2010 038 544

(51) Int. Cl.
*G01N 23/04* (2006.01)
*G01N 23/083* (2006.01)
(Continued)

(52) U.S. Cl.
CPC ................. *G01N 23/04* (2013.01); *A61J 3/074* (2013.01); *B65B 1/46* (2013.01); *B65B 3/003* (2013.01);
(Continued)

(58) Field of Classification Search
CPC ....... G01N 23/04; G01N 23/06; G01N 23/08; G01N 23/083; G01N 23/087; G01N 23/10; G01N 23/12; G01N 2223/04; G01N 2223/601

USPC ............................ 378/51, 53, 54, 56, 57, 207
See application file for complete search history.

(56) References Cited

U.S. PATENT DOCUMENTS

| 709,598 A | 9/1902 | Gray |
| 3,709,598 A | 1/1973 | Vandenberg et al. |

(Continued)

FOREIGN PATENT DOCUMENTS

| CN | 1551754 | 12/2004 |
| CN | 101365410 | 2/2009 |

(Continued)

OTHER PUBLICATIONS

PCT/EP2010/064616 International Search Report dated Apr. 18, 2011 (Translation and Original, 12 pages).

(Continued)

*Primary Examiner* — Allen C. Ho
(74) *Attorney, Agent, or Firm* — Michael Best & Friedrich LLP

(57) ABSTRACT

The invention relates to a sensor device (30; 30a; 30b; 30c) for a packaging machine (100) designed as a capsule filling and sealing machine or for a capsule control device (100a), said device having a positioning element (35; 35a) for positioning a container (c) having a longitudinal axis (15) and filled with a filling material in the region of the sensor device (30; 30a; 30b; 30c) and at least one radiation source (31; 31 a; 3 b) and at least one detector (40; 40a; 40b) for detecting the radiation after said radiation radiates through the container (c). According to the invention, the at least one radiation source (31; 31a; 31b) radiates through the container (c) perpendicular to the longitudinal axis (15) thereof and the positioning element is designed as a tubular or shaft-shaped conveying element (35; 35a) which can be penetrated by the radiation in a radiation cone (38) of the radiation source (31; 31a; 31b).

12 Claims, 6 Drawing Sheets

Figure 1:
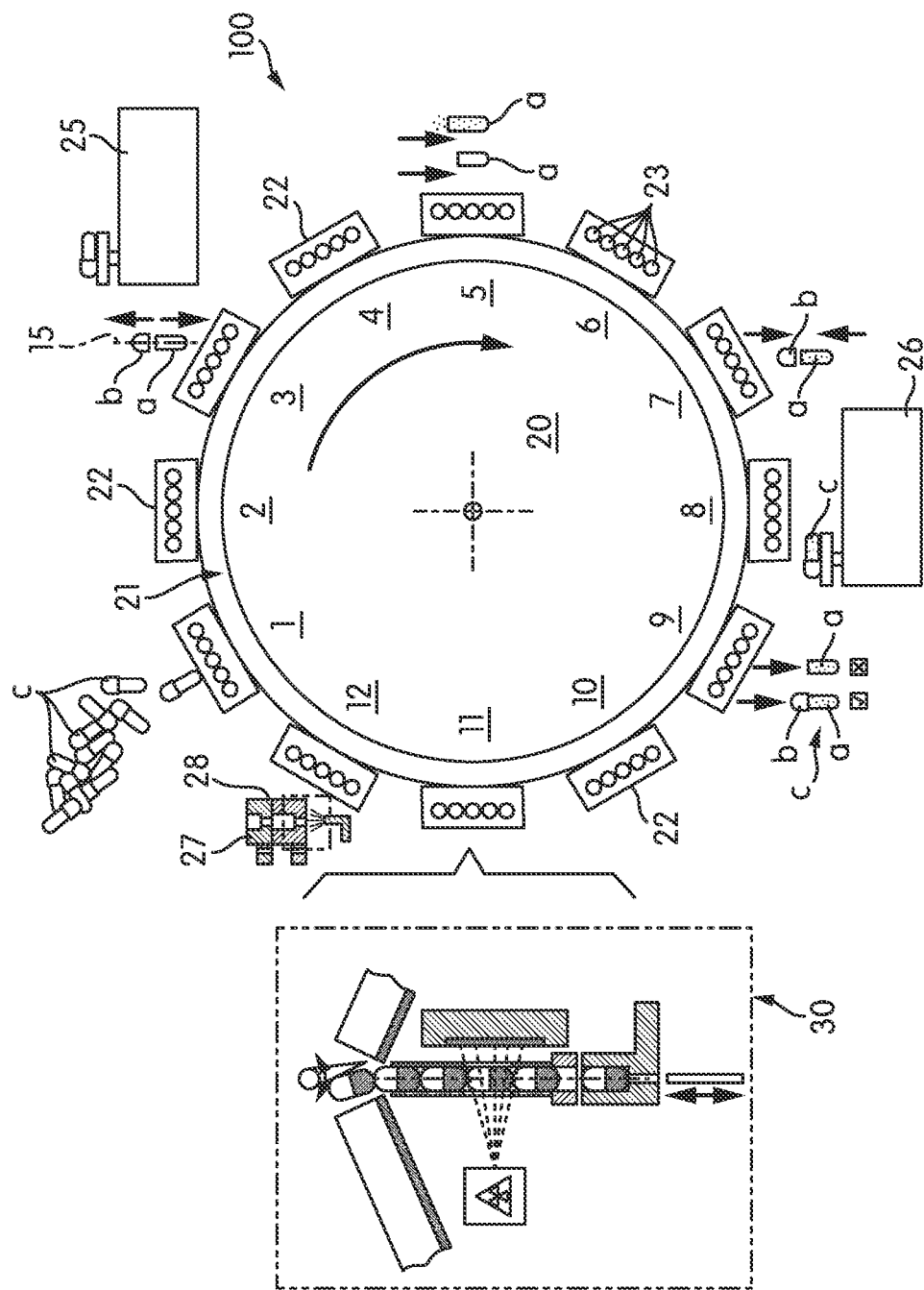

(51) Int. Cl.
  *G01N 23/087* (2006.01)
  *G01N 23/06* (2006.01)
  *G01N 23/10* (2006.01)
  *A61J 3/07* (2006.01)
  *B65B 1/46* (2006.01)
  *B65B 3/00* (2006.01)
  *B65B 57/14* (2006.01)

(52) U.S. Cl.
  CPC .............. *B65B 57/145* (2013.01); *G01N 23/06* (2013.01); *G01N 23/083* (2013.01); *G01N 23/087* (2013.01); *G01N 23/10* (2013.01); *G01N 2223/04* (2013.01); *G01N 2223/601* (2013.01)

(56) References Cited

U.S. PATENT DOCUMENTS

| | | | |
|---|---|---|---|
| 4,117,935 A | | 10/1978 | Richardson et al. |
| 4,330,835 A | * | 5/1982 | Gehm ........................... 702/172 |
| 4,695,729 A | * | 9/1987 | Monno et al. ............... 250/358.1 |
| 5,042,055 A | * | 8/1991 | Wirt et al. ........................ 378/59 |
| 5,420,427 A | * | 5/1995 | Morgan et al. .............. 250/360.1 |
| 5,614,720 A | * | 3/1997 | Morgan et al. .............. 250/360.1 |
| 5,687,210 A | * | 11/1997 | Maitrejean et al. ............. 378/57 |
| 5,864,600 A | | 1/1999 | Gray et al. |
| 5,917,876 A | * | 6/1999 | Fujii et al. .......................... 378/4 |
| 6,162,998 A | | 12/2000 | Wurst et al. |
| 6,201,850 B1 | * | 3/2001 | Heumann ........................ 378/56 |
| 6,377,654 B1 | * | 4/2002 | Willems et al. .................. 378/59 |
| 6,872,949 B2 | * | 3/2005 | Mizuoka et al. ............ 250/358.1 |
| 6,925,145 B2 | * | 8/2005 | Batzinger et al. ................ 378/59 |
| 7,656,997 B1 | * | 2/2010 | Anjelly ............................ 378/59 |
| 7,727,567 B2 | * | 6/2010 | Heuft .............................. 426/232 |
| 7,792,247 B2 | * | 9/2010 | Schmied et al. ................. 378/54 |
| 7,885,381 B2 | * | 2/2011 | Nagumo et al. ................. 378/59 |
| 8,266,874 B2 | * | 9/2012 | Runft et al. ...................... 53/432 |
| 2004/0249591 A1 | | 12/2004 | Trebbi |
| 2008/0134629 A1 | | 6/2008 | Schmied et al. |

FOREIGN PATENT DOCUMENTS

| DE | WO 2006/106012 A1 | * | 10/2006 | ................ B65B 1/30 |
|---|---|---|---|---|
| DE | WO 2007/062947 A1 | * | 6/2007 | ................ A61J 3/07 |

OTHER PUBLICATIONS

Meng Xiang-cheng, "Explosives and narcotic detection technologies" Nuclear Electronics&Detection Technology vol. 23, No. 4, 2003, pp. 371-379, 363.

Liu Shu, "X-ray security detection technology," Journal of Chinese Peoples's Public Security University, No. 4, 2008, pp. 78-80.

Pan Ligang, "Review on non-destructive determination technology for agricultural product quality" transactions of the CSAE, vol. 24, 2008, pp. 325-330.

* cited by examiner

SENSOR DEVICE FOR A PACKAGING MACHINE DESIGNED AS A CAPSULE FILLING AND SEALING MACHINE OR FOR A CAPSULE CONTROL DEVICE

BACKGROUND OF THE INVENTION

The invention relates to a sensor apparatus for a packaging machine, which is in the form of a capsule filling and closing machine, or for a capsule monitoring apparatus.

A sensor apparatus such as this is known from DE 10 2005 016 124 A1. The known sensor apparatus is arranged in the area of a capsule filling and closing device and has an X-ray radiation source which passes radiation through containers in the longitudinal direction, which containers are filled with a filling material, for example a pharmaceutical product in the form of powder. A detector is arranged on the side of the container opposite the X-ray radiation source, measures the X-ray radiation after it passes through the container, and supplies this in analog form to an evaluation device. In particular, the weight of the filling material in the containers is determined by means of the sensor apparatus that is so far known.

This has the disadvantage that, because the containers are arranged in step-like holding holes in holding segments, when the radiation is passed through the containers, their entire cross section is not detected, with a portion of the cross section instead being covered by the holding hole. The result is therefore dependent on the geometry of the holding hole, and the measurement result may be corrupted. Additional statements can be made only with difficulty, if at all, because radiation is passed through the containers in the direction of the longitudinal axis of the containers, since the radiation passes through only a relatively limited area of the container.

DE 198 19 395° C.1, from the same applicant, discloses a weighing device for weighing hard-gelatin capsules, which has a feed element in the form of a flywheel which in each case moves a capsule into the area of a weighing goods holder, which is arranged in a suspended manner, and feeds the capsule on further therefrom.

U.S. Pat. No. 5,864,600 discloses an image-processing monitoring device, in which the filling level in containers is checked by means of a beam source, with the beam passing through the containers at right angles to their container longitudinal axis. The containers are in this case arranged at a distance from one another on a horizontally arranged feed device.

SUMMARY OF THE INVENTION

In the light of the described prior art, the invention is based on the object of developing a sensor apparatus for a packaging machine, which is in particular in the form of a monitoring device or a capsule filling and closing device, such that its measurement accuracy is improved, and further conclusions relating to the container and its filling material are made possible in a simple manner. The sensor device is intended to have a high performance and to be to feed and to position the capsules easily in the area of the sensor device. In this case, the invention is based on the idea that, by passing radiation through the container at right angles to its longitudinal axis, this allows radiation to be passed through a greater area of the container, and allows a greater area of the container to be detected, thus allowing a quantitatively and quantitatively better statement to be made about said characteristics. Furthermore, the positioning element, which is tubular or in the form of a shaft and through which the radiation lobe from the beam source can pass makes it possible to position the capsules very easily and at the same time precisely in the area of the sensor device.

In one preferred embodiment of the invention, an X-ray radiation source is provided as the radiation source. An X-ray radiation source not only makes it possible to detect the filling weight of the container in a simple manner, but also, for example, makes it possible to detect the filling height in the container and damage to the container, or the like.

Furthermore, in order to improve the performance of the apparatus and to reduce the hardware complexity, the invention particularly preferably provides for a plurality of feed elements to be arranged parallel to one another, and for a plurality of feed elements to be arranged such that they are operatively connected to a common radiation source and to a common detector. A plurality of containers can thus each be checked in one step at the same time, by means of a single radiation source and by means of a single detector.

One feed option for the containers whose design is simple, in the area of the radiation source, and which at the same time prevents corruption of the measurement results by parts of the apparatus, is achieved in that the containers are arranged stowed in a row in the feed element, and are fed by mutual touching contact of the containers at least in the area of the sensor apparatus.

It is particularly preferable if the detector is in the form of an image-evaluating detector and interacts with an evaluation device which allows digital data evaluation. This makes it possible to produce various parameters and measurement results from the signals and recordings obtained, in a simple manner.

In order to achieve accurate measurement, particularly of the weight of a capsule, the invention preferably provides that the at least one radiation source is additionally arranged such that it is operatively connected to a reference object, and that the detector at the same time additionally detects the image of the reference object, in addition to the image of the container, and supplies this to the evaluation device. The image of the container and/or of the capsule is therefore always related to the reference object, thus precluding absolute fluctuations between two successive images, which would lead to corruption of the measurement result.

In this case, in order to improve the measurement accuracy and to simplify the evaluation, it is particularly advantageous and necessary that the reference object is composed of a material which at least approximately has the same absorption characteristics for the radiation, in particular for the X-ray radiation, as the container.

In order to ensure that accurate and correct measurement results are achieved over the entire tolerance range of the characteristic to be measured, it is furthermore essential that the reference object has areas of different absorptions for the radiation, with at least one area being provided whose absorption, within the tolerances of the characteristic of the container to be measured, is less than the minimum absorption of the container, and an area whose absorption, within the tolerances of the characteristic of the container (c) to be measured, is greater than the maximum absorption of the container.

One advantageous refinement, which can be manufactured easily, of the reference object, in which the information relating to the reference object can be processed easily by means of the evaluation device, is made possible if the reference object is in the form of a wedge or step, and if the reference object is arranged such that the thickness of the reference object varies in the radiation direction of the radiation source.

In a further design refinement of the invention, the sensor device is followed by a weighing device which has at least one weighing cell for weighing the container. A refinement such as this provides a second monitoring option for the containers, as a result of which not only is the X-ray image used for evaluation and/or qualitative or quantitative detection of the container, but also the weighing device. In addition, this allows duplicated monitoring of the filling weight, as a result of which the two measurement results can be compared with one another, and a faulty test device can be deduced if they do not match. The claimed sensor apparatus for a packaging machine therefore operates particularly safely and reliably.

BACKGROUND OF THE INVENTION

Figure 2:
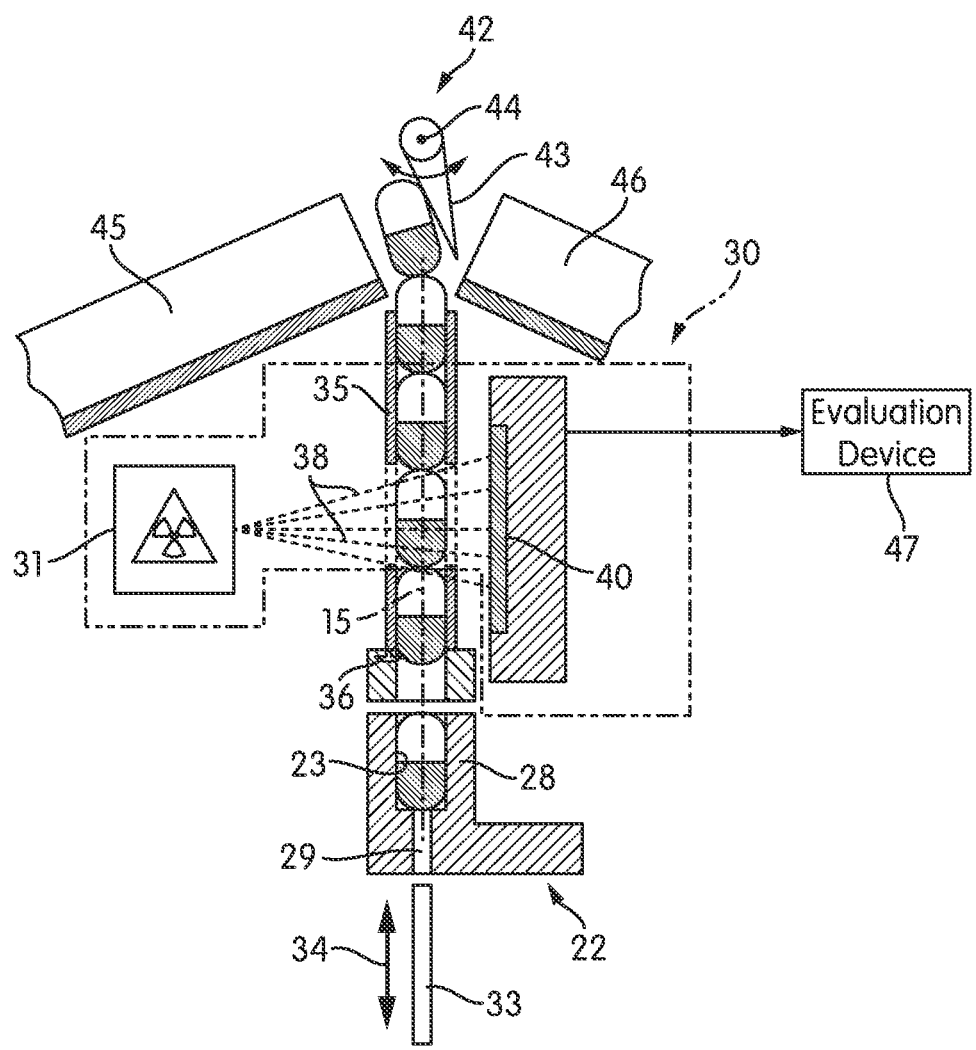
Figure 3:
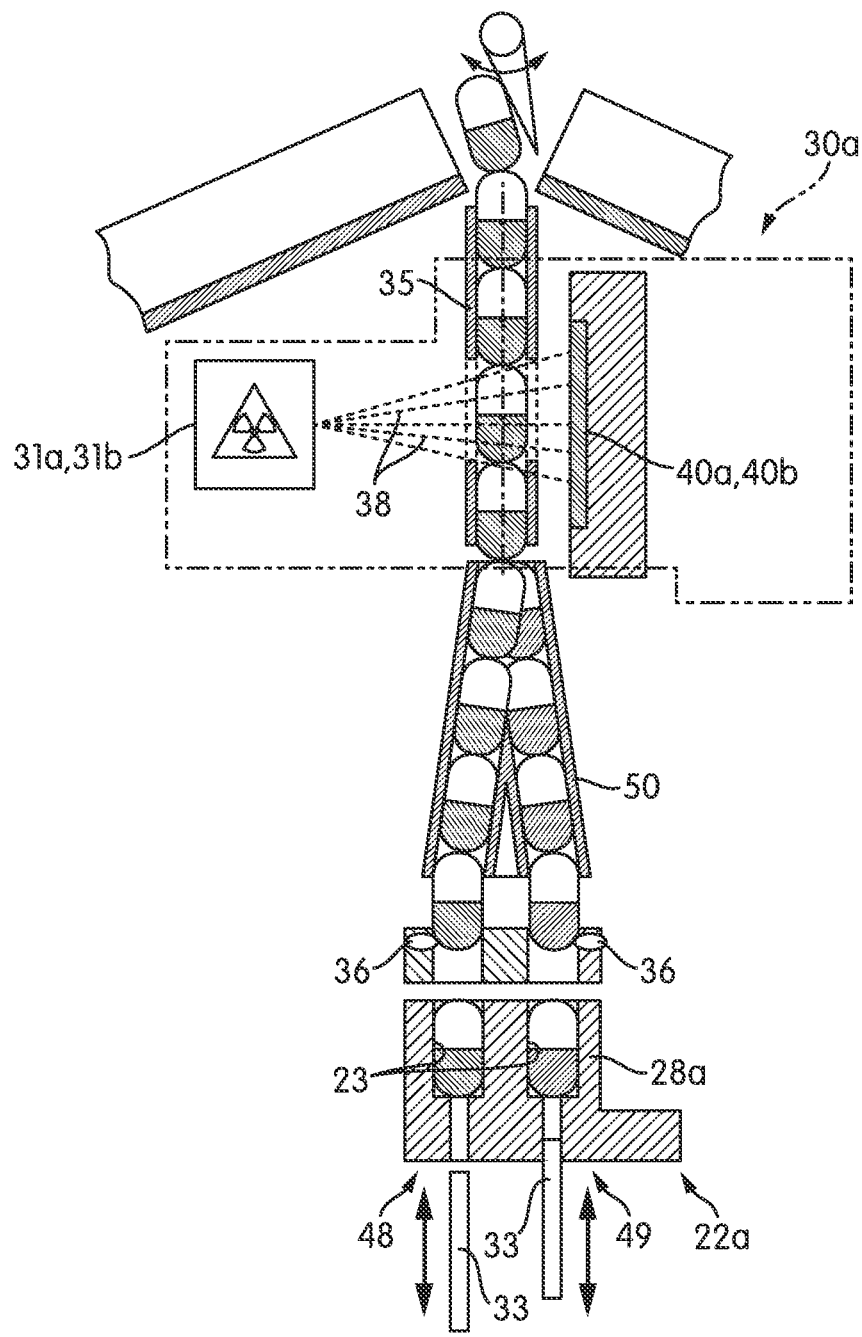
Figure 4:
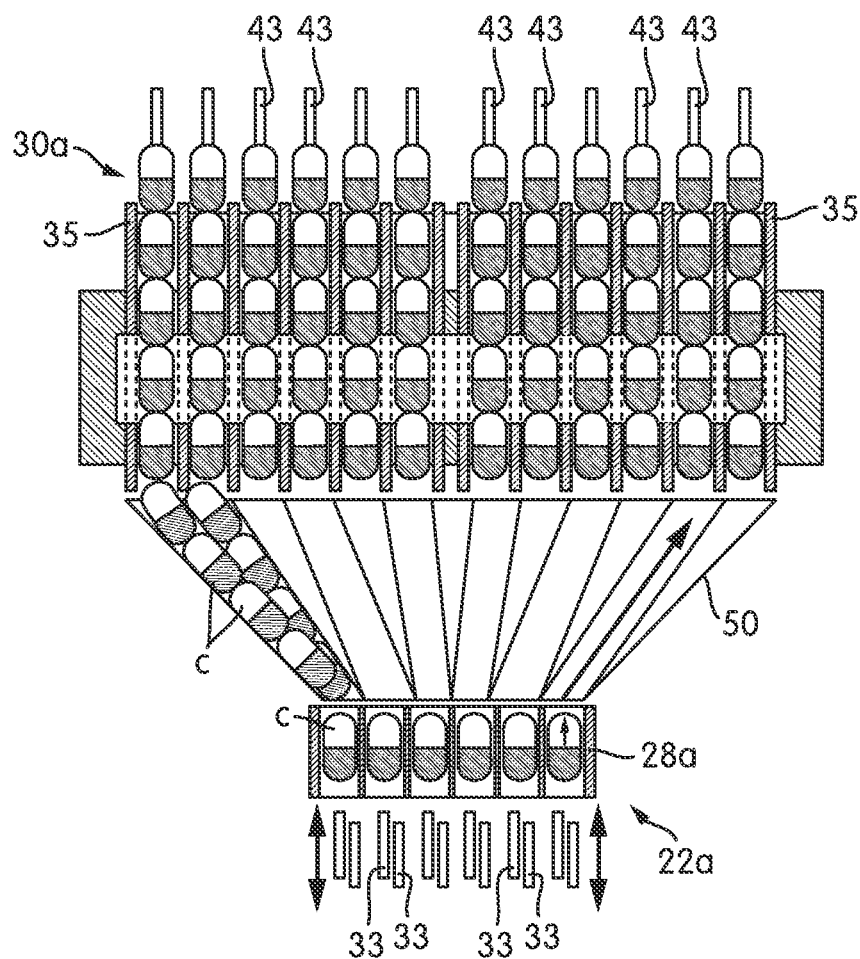
Figure 5:
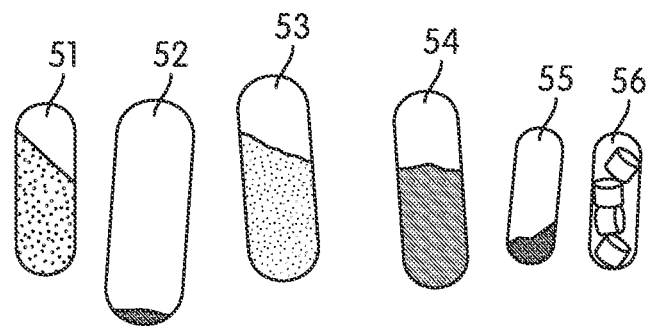
Figure 6:
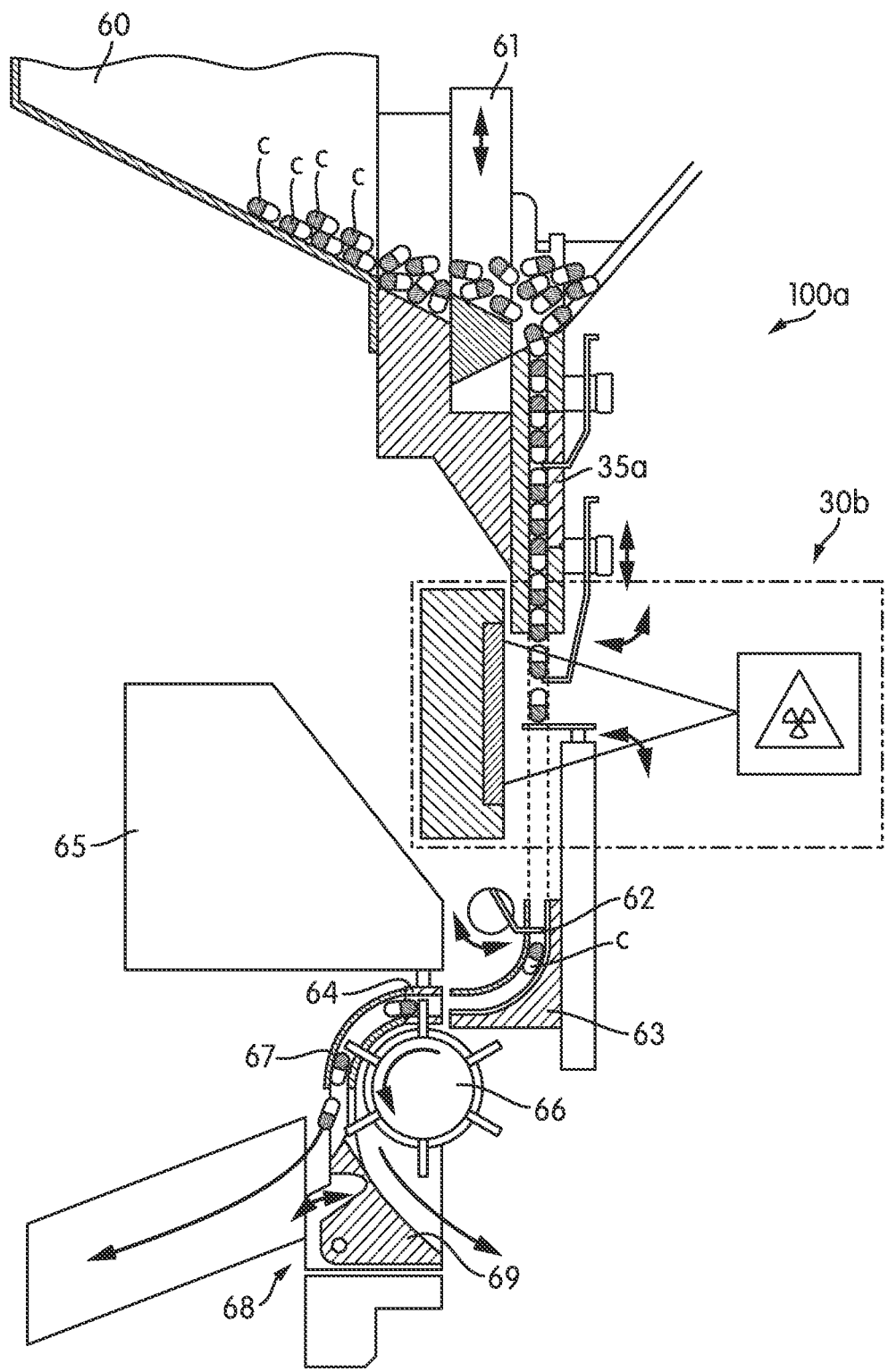
Figure 7:
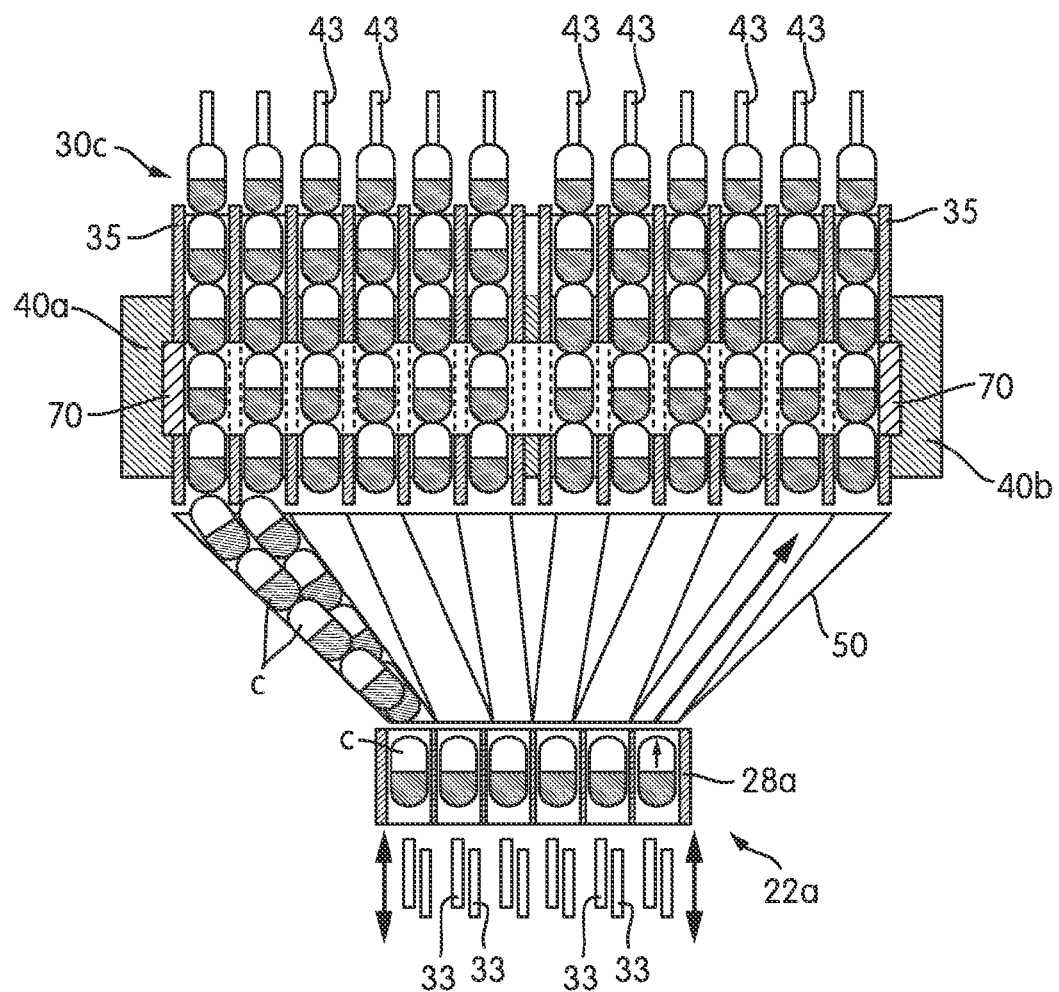
Figure 8:
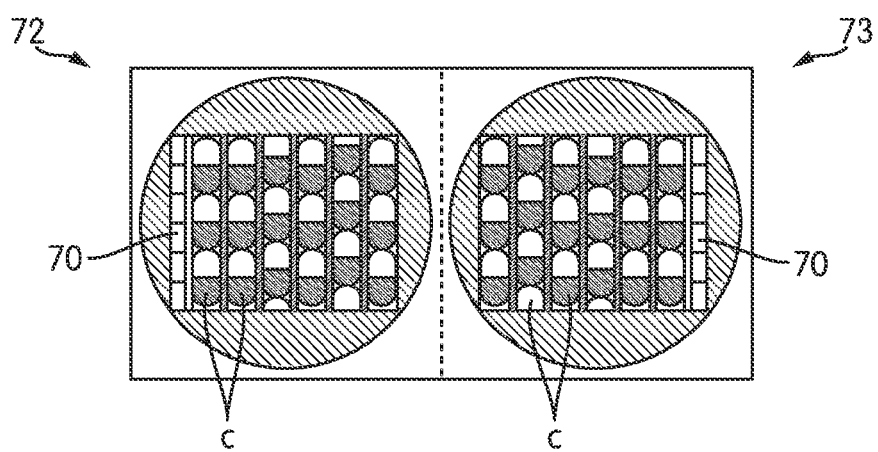

Further advantages will become evident from the following description of preferred exemplary embodiments and from the drawings, in which:

FIG. 1 shows a simplified plan view of a capsule filling and closing machine,

FIG. 2 shows a sensor apparatus according to the invention, as used for a packaging machine as shown in FIG. 1, in the form of a schematic side view and partially sectioned, FIG. 3 shows a modified sensor apparatus using holding sections, in which two rows of capsules are in each case fed, FIG. 4 shows a simplified front view of the sensor apparatus as shown in FIG. 3, FIG. 5 shows examples of images recorded by means of an apparatus according to the invention and which are supplied to a digital evaluation device for evaluation, FIG. 6 shows a simplified longitudinal section through a monitoring device for capsules, FIG. 7 shows a simplified side view of a capsule filling and closing machine which has been modified in comparison to FIGS. 3 and 4, and FIG. 8 shows examples of images which have been recorded by means of the capsule filling and closing machine as shown in FIG. 7, which images supplied to a digital evaluation device for evaluation.

The same components are provided with the same reference number in the figures.

DETAILED DESCRIPTION

FIG. 1 shows a packaging machine in the form of a capsule filling and closing machine 100. The capsule filling and closing machine 100 has a feed wheel 21 which is rotated in steps on a vertical axis 20. The capsule filling and closing machine 100 is used for filling and closing capsules c, which consist of a capsule lower part a and a plugged-on cap b. In this case, the capsule c forms a container, which is elongated overall, with a longitudinal axis 15 for a filling material, which in particular is a pharmaceutical product or the like in the form of pieces or powder.

The feed wheel 21 has stations 1 to 12 which are arranged on the circumferential path of the feed wheel 21 and at which handling devices are arranged. The capsule filling and closing machine 100 which has been described so far is in the form of a standardized packaging machine, as a result of which there is no need to arrange handling devices at all of the stations 1 to 12, depending on the application. Furthermore, twelve holding segments 22, which consist of an upper part 27 and a lower part 28 (see station 12) are arranged at uniform angular intervals on the external circumference of the feed wheel 21, for in each case five capsules c, which are arranged in a row. The holding segments 22 are format parts, which can be replaced on the feed wheel 21, depending on the desired application and depending on the format of the capsules c being processed.

In order to hold the capsules c, each holding segment 22 in the exemplary embodiment has five holding holes 23 in the upper part 27 and in the lower part 28. However, holding segments 22 with more than five holding holes 23 arranged in a row, and with more than one row of holding holes 23, are also possible. The empty capsules c to be filled up are passed in an unorganized form to the station 1, are aligned, and are supplied in an organized form to the feed wheel 21. The caps b are then separated from the capsule lower parts a in the area of the station 3 and both are weighed, if required in advance on a sample basis, by a weighing device 25 in order to determine their net weight. In the station 4, the caps b except for the cover are then fitted to the capsule lower parts a (not illustrated) thus allowing the capsule lower parts a to be filled with filling material in the station 5. In the area of the station 7, the caps b are once again moved to cover the capsule lower parts a and, in the station 8, individual capsules c are weighed on a sample basis on a further weighing device 26 process which is gross weighing. In the area of the station 9, the capsules c are checked for the presence of their caps b, with capsules c and individual capsule lower parts a and caps b being ejected in the area of the station 10. A sensor apparatus 30 according to the invention is arranged in the area of the station 11. Finally, the holding segments 22, which have in the meantime been emptied, are cleaned, in particular by means of airblast, in the area of the station 12.

By way of example, reference is furthermore made with respect to the precise operation of a capsule filling and closing machine such as this to DE 10 2005 016 124 A1, from the same applicant, which describes further details relating to the fundamental operation and method of operation thereof.

As can be seen in particular in FIG. 2, the sensor apparatus 30 is arranged above the lower parts 28 of the holding segments 22. The sensor apparatus 30 operates by means of a radiation source, which is in the form of an X-ray radiation source 31.

In addition, it should be mentioned, however, that the invention can also in principle operate using different optical inspection processes, for example by means of a through-lighting process with a light source and a camera.

An ejector pin 33 is arranged underneath the lower parts 28 of the holding segments 22 for each holding hole 23 and aligned with the holding holes 23, which ejector pin 33 can be moved up and down as indicated by the double-headed arrow 34, and is aligned with an aperture hole 29 in the lower part 28. A feed element 35 which is tubular or in the form of a shaft is associated with each holding hole 23, above and aligned with the holding holes 23 in the holding segments 22. The longitudinal axis of the feed element 35 is aligned essentially vertically and, at its end facing the holding segment 22, in each case has a respective clamping piece 36 for each holding hole 23, which prevents the lowest capsule c from falling out of the feed element 35 back in the direction of the holding hole 23.

The X-ray radiation source 31 emits an X-ray radiation lobe 38, which can be detected by means of a detector 40, which records and/or processes images, operates in particular digitally, is in the form of an X-ray large-area-sensor and is located on the opposite side of the capsule c to the X-ray radiation source 31.

In order to prevent disturbances in the detection of the X-ray radiation lobe 38 in the area of the detector 40 by the feed element 35, the feed element 35 is designed with suitable measures (for example by means of a plastic design) to allow X-ray radiation to pass through in the area of the X-ray radiation lobe 38, and it is intended to be expressed by the dashed-line representation of the feed element 35 in the area of the X-ray radiation lobe 38. Furthermore, according to the invention, it is important that the clamping piece 36 and the feed element 35 are arranged with respect to the X-ray radiation lobe 38 such that, as is shown in FIG. 2, a capsule c is located completely in the radiation lobe 38 when the lowest of the capsules c, which are positioned one above the other as a row, is held by the clamping piece 36. An appropriate optic and/or an appropriate arrangement (separation) of the feed element 35 with respect to the X-ray radiation source 31 furthermore ensure that, as far as possible, the X-ray radiation lobe 38 does not cover any areas of capsules c below or above the capsule c that is currently being X-rayed. If this nevertheless were to occur, for example because of tolerances in the length of the capsules c, then, if appropriate, this can be compensated for by appropriate software in the evaluation device 47, which will be mentioned further below. According to the invention, the feed element 35 is arranged with respect to the X-ray radiation source 31 and with respect to the X-ray radiation lobe 38 such that the X-ray radiation lobe 38 passes through the capsule c at right angles to its longitudinal axis 15, which means that the detector 40 can record an image corresponding to a longitudinal section through the capsule c.

The detector 40 and the X-ray radiation source 31 are designed and arranged such that a plurality of capsules c, which are arranged alongside one another at one level, can each be X-rayed by them at the same time, and the X-ray radiation lobe 38 can be detected by the detector 40.

In the exemplary embodiment illustrated in FIGS. 1 and 2, five capsules c are in each case arranged in a row in the holding segments 22. The sensor apparatus 30 can therefore be used to simultaneously examine all five capsules c in each case in one test step during a phase when the capsules c are stationary in the feed element 35.

A segregation device 42 is arranged above the feed element 35. The segregation device 42 comprises a separately controllable segregation flap 43 for each of the feed elements 35, which segregation flap 43 is mounted such that it can pivot on an axis 44 and, depending on the position of the segregation flap 43, segregate individual capsules c in the direction of a good shaft 45 and a bad shaft 46.

The sensor apparatus 30 which has been described so far for the capsule filling and closing machine 100 operates as follows: the feed wheel 21 transports the holding segments 22 cyclically below the area of the sensor apparatus 30. In a phase when the feed wheel 21 is stationary, the capsules c which are located in the holding segment 22 are pushed synchronously by means of the ejector pins 33 out of the holding holes 23 in the lower part 28 of the holding segment 22, upwards in the direction of the feed elements 35. In the process, the capsules c which have in each case been pushed out previously still each rest on the clamping pieces 36 and, when subsequent capsules c are pushed in, are shifted further upwards by touching contact between the capsules, by one capsule length in each case. Because of the geometry of the feed elements 35, capsules c are each still located exactly within the X-ray radiation lobe 38 of the X-ray radiation source 31. During a phase in which the feed elements 35 are stationary, that is to say when no capsules c are currently being pushed over into the feed element 35 at an instant, the detector 40 in each case records an image of the capsules c which are located within the X-ray radiation lobe 38, and supplies this to an evaluation device 47. The evaluation device 47 allows digital evaluation and storage of the recorded image of the X-ray radiation lobe 38. Once the evaluation device 47 has examined the recorded image for the desired characteristics, in particular with regard to the filling weight, any capsules c which have been identified as "bad capsules c" can be sorted out by means of the segregation device 42.

By way of example, FIG. 5 shows six different recordings 51 to 56, recorded by a detector 40 alongside one another of capsules c filled with different filling materials and of different sizes. Different filling materials and different filling levels and arrangements of the filling materials in the capsules c can be seen in these recordings 51 to 56. The evaluation program in the evaluation device 47 allows the sensor apparatus 30 to determine not only the respective filling weight of the capsule c, but also in addition to carry out further evaluations. By way of example, the status of the capsule casing (which means identification of defects in the capsule casing, such as cracks, fractures, pinches, deformations, etc.) may be mentioned. It is also possible to detect the state of the filling material, for example whether a pressed item is intact or has been destroyed, or whether a tablet is broken, etc. In principle, the capsule c can also be checked for the presence of the product. By way of example, this includes counting down tablets, microtablets or capsules in the capsule c, or their combinations. In principle, of course, it is also possible to identify capsules c which have not been filled or have been filled incorrectly. By way of example, mention should finally be made of the fact that the capsules c can also be examined for foreign bodies (in particular metal particles). In this case, it is particularly advantageous that the capsule c is detected completely, that is to say over its entire longitudinal extent, by the X-ray radiation lobe 38, because of the arrangement and configuration of the feed elements 35, without the capsules c in the process being concealed by parts of the feed elements 35 when lateral guides for the capsules c in the feed elements 35 may, for example, be composed of plastic.

FIGS. 3 and 4 show a modified sensor apparatus 30a. In this case, holding segments 22a and lower parts 28a are provided which, in contrast to the holding segments 22, have two rows 48, 49 of holding holes 23 for capsules c. As can be seen in particular from FIG. 4, six capsules c are in each case arranged within one holding segment 22a in each of the rows 48 and 49 in this case. In order nevertheless to make it possible to test the greater number of capsules c, in comparison to the holding segment 22, in a single test step, provision is made for the capsules c to be pushed over into the individual feed elements 35 by means of a funnel-shaped distributor 50, such that all twelve capsules c are arranged alongside one another on one plane, as can be seen in particular in FIG. 4. Because of the relatively large area of the capsules c which are arranged alongside one another, it may be necessary to use a plurality of X-ray radiation sources 31a, 31b as well as a plurality of detectors 40a, 40b, which are arranged at right angles to the plane of the drawing in FIG. 3.

FIG. 6 shows a capsule monitoring apparatus 100a. The capsule monitoring apparatus 100a may in this case be a component of an already described capsule filling and closing machine 100, or may be operated as a separate monitoring apparatus 100a. A filling material container 60 with capsules c which have already been filled and closed is provided for the capsule monitoring apparatus 100a. The capsules c are separated from the filling material container 60 by means of a slide 61 which can be moved up and down, and are supplied to the feed element 35a in a row (or else in a plurality of rows arranged at right angles to the plane of the drawing in FIG. 6). A sensor apparatus 30b is arranged under the filling material container 60, the function of which sensor apparatus 30b has already been explained within the description of the capsule filling and closing machine 100 as shown in FIGS. 1 to 5. In particular, the sensor apparatus 30b can be used to detect the filling weight and possible damage to and contamination of the capsules c.

A blocking latch 62 is provided under the sensor apparatus 30b on the feed element 35a and in each case releases a capsule c which has previously been examined in the area of the sensor apparatus 30b, or blocks it. Following the blocking latch 62, the feed element 35a has a curved section 63 at whose outlet, and aligned with it, a weighing cell 64, which is arranged in suspended form, is arranged. The weighing cell 64 is a component of a weighing device 65, whose exact design and method of operation has already been explained in detail in DE 198 19 395 C1, from the same applicant, and to which reference is therefore made.

In particular, the weighing device 65 has an impeller wheel 66 which is moved in steps in the counterclockwise direction and with whose aid one capsule c is in each case fed into the area of the weighing cell 64, and out of it. The weighing device 65 is followed, via a further curved area 67, by an additional ejection device 68, which has a moving flap 69. The flap 69 makes it possible to separate good capsules c from bad capsules c depending on the result of the evaluations, in the area of the sensor apparatus 30b and of the weighing device 65.

In addition, it should be mentioned that the capsule monitoring apparatus 100a can also be modified such that no filling material container 60 is provided. In this case, the weighing device 65 follows the sensor apparatuses 30 and 30a, as shown in FIGS. 1 to 3, and is connected thereto. In other words, this means that a dedicated, separate impeller wheel 66 can be provided for each of the feed elements 35a, with the weighing device 65 then likewise having a dedicated weighing cell 64 for each feed element 35a.

FIG. 7 shows a sensor apparatus 30c, which has once again been modified in comparison to FIGS. 3 and 4. In the sensor apparatus 30c, a reference object 70 is arranged on each of the two opposite sides in the beam path of the X-ray radiation source (which is not illustrated). Two (identical) reference objects 70 are arranged with a view to in each case detecting and checking six capsules c, in each case by means of a detector 40a, 40b. A reference object 70 is therefore associated with each detector 40a, 40b. An important factor in this case is that, when using X-rays, the reference object 70 consists of a material which is as similar as possible to the atomic composition of the material to be analyzed, that is to say the material of the capsule c and the capsule content. Furthermore, provision is advantageously made for the reference object 70 to be in the form of a wedge or step. In this case, the reference object 70 is arranged such that the height of the reference object 70, which is in the form of a wedge or step, varies in the direction in which the radiation from the X-ray radiation source 31 passes through. A further important factor is that the attenuation of the X ray radiation by the reference object 70, at least in one area of the reference object 70, is greater than the greatest attenuation caused by the capsule c (this is dependent on the density, the atomic composition and the thickness of the filling material and capsule c through which the radiation passes). Furthermore, the attenuation of the X-ray radiation by the reference object 70 at another point or on another area of the reference object 70 must be less than the smallest attenuation caused by the capsule c. In this case, any desired number of steps may be implemented between the two attenuation areas mentioned by the reference object 70 being in the form of a wedge or step. FIG. 8 shows two images 72, 73, which have been detected by means of two detectors 40a, 40b and are fed to the evaluation device 47, with one reference object 70, which is in the form of a step or staircase, being used in each case.

In order to adjust the detectors 40a, 40b, it is necessary to be able to remove the reference object 70 from the image 72, 73. Furthermore, it is essential that the position and orientation of the reference object 70 does not change during operation of the sensor apparatus 30c. For starting up, the X-ray camera system, consisting of the X-ray radiation source 31, 31a and 31b and the detector 40, 40a and 40b, is first of all adjusted without the reference object 70. A reference object 70 and an object to be measured, that is to say a capsule c, are then measured and an image 72, 73 is recorded. This image 72 or 73 is stored. Radiation is then optionally passed through a second object to be measured and a second capsule c to be measured, and an image 72, 73 is recorded and stored. The capsule c is then located in the image 72, 73. The grayscales of the reference object 70 are read and are linked or related to the actual geometric dimensions of the reference object 70. The object to be measured, that is to say the capsule c to be measured, is then located in the image 72, 73, and its information (for example individual grayscale values, area of the object on the image, etc.) is read by means of the evaluation device 47 from the image 72, 73. This object information (for example grayscale values) is converted pixel-by-pixel to a virtual thickness, to be precise using the information from the reference object 70. The mean value of these virtual individual thicknesses within the selected area can now be associated with the actual gravimetric weight of the capsule c, which was determined using a gravimetric weighing device. The reference object 70 is then located in the second image 72, 73. The grayscales of the reference object 70 are likewise read and are compared with the grayscale values of the reference object 70 from the first image. If the grayscale values of the (second) reference object 70 are within a defined limit, the second recorded image 72, 73 is not corrected. If there is a change in the information, for example the grayscale values of the second reference object 70 outside defined limits, the image 72, 73 is appropriately corrected. The object (capsule c) to be measured is then located analogously to the manner in the first image 72, 73, and its information is read from the image 72, 73. In this case as well, the object information is then converted pixel-by-pixel to a virtual thickness, to be precise with the aid of the information from the reference object 70. The mean value of these virtual individual thicknesses can now be associated with the actual gravimetric weight of the measurement object. If a third object to be measured and a third capsule c to be measured as well as the reference object 70 are now inserted into the X-ray camera system, the system is able to use the information from the two images 72, 73, the reference object 70 and the gravimetric weights from the first two weighing processes to determine the weight of the third object (and of any desired number of further objects).

The capsule filling and closing machine 100 described so far and the capsule monitoring apparatus 100a can be modified in many ways. However, it is essential to the invention that the radiation sources are arranged with respect to the containers which pass through radiation such that radiation is passed through them at right angles to their longitudinal direction.

The invention claimed is:
1. A sensor apparatus for a packaging machine, the sensor apparatus comprising:
   a sensing area;
   at least one positioning element for positioning a container in the sensing area, the container configured to be filled with a filling material and having a longitudinal axis;
   a restraint element;
   at least one X-ray radiation source configured to generate a radiation, the at least one X-ray radiation source configured to pass the radiation through the container at a right angle to the longitudinal axis;
   at least one detector for detection of the radiation;

an evaluation device that is configured to perform digital data evaluation;

wherein the at least one positioning element is in the form of a feed element, which is tubular or in the form of a shaft, and through which the radiation can pass in a radiation lobe from the at least one X-ray radiation source, and the feed element is radiolucent in at least the sensing area; and wherein the feed element is aligned essentially vertically and the restraint element is associated with the feed element and prevents the container from falling out of the feed element; and wherein the at least one detector is arranged opposite the at least one X-ray radiation source and detects the radiation from the at least one X-ray radiation source after the radiation has passed through the container, and the at least one detector is in the form of an image-evaluating detector and interacts with the evaluation device.

2. The sensor apparatus as claimed in claim 1, wherein the at least one positioning element includes a plurality of positioning elements arranged substantially parallel to one another, and wherein at least some of the plurality of positioning elements are arranged to be operatively connected to a common X-ray radiation source that is at least one of the at least one X-ray radiation source and to a common detector that is at least one of the at least one detector for detection.

3. The sensor apparatus as claimed in claim 1, wherein the feed element is configured to feed a plurality of containers, the plurality of containers arranged stowed in a row, and fed by mutual touching contact of two or more of the plurality of containers at least in the sensing area.

4. The sensor apparatus as claimed in claim 3, further comprising a holding segment and a pushing element, wherein the feed element is arranged above the holding segment for the plurality of containers, from which the plurality of containers are pushed over into the feed element by the pushing element.

5. The sensor apparatus as claimed in claim 1, wherein the feed element is configured to cyclically feed a plurality of containers into the sensing area of the at least one radiation source, and the at least one detector, for each of the plurality of containers, detects the radiation in the feed element in a stationary phase of each one of the plurality of containers.

6. The sensor apparatus as claimed in claim 5, wherein the at least one X-ray radiation source and the at least one detector are configurable to detect a filling weight or another characteristic of the container.

7. The sensor apparatus as claimed in claim 1, further comprising a weighing device positioned downstream of the sensing area, wherein the weighing device has at least one weighing cell for weighing the container.

8. The sensor apparatus as claimed in claim 7, wherein the weighing device has a feed and blocking element, which feeds a container from the feed element into the weighing cell and out of the weighing cell.

9. The sensor apparatus as claimed in claim 1, further comprising a reference object, wherein the at least one X-ray radiation source is additionally arranged such that the at least one X-ray radiation source is operatively connected to the reference object, and in that the at least one detector at the same time additionally detects an image of the reference object, in addition to an image of the container, and supplies this to the evaluation device.

10. The sensor apparatus as claimed in claim 9, wherein the reference object is composed of a material which at least approximately has the same absorption characteristics for the radiation as the container.

11. The sensor apparatus as claimed in claim 9, wherein the reference object has areas of different absorptions for the radiation, with at least one area being provided whose absorption, within the tolerances of the characteristic of the container to be measured, is less than the minimum absorption of the container, and an area whose absorption, within the tolerances of the characteristic of the container to be measured, is greater than the maximum absorption of the container.

12. The sensor apparatus as claimed in claim 11, wherein the reference object is in the form of a wedge or step, and in that the reference object is arranged such that a thickness of the reference object varies in the radiation direction of the at least one X-ray radiation source.

* * * * *